United States Patent
Gordon et al.

[11] Patent Number: 6,033,418
[45] Date of Patent: Mar. 7, 2000

[54] METHOD AND DEVICE FOR CORNEAL SHAPING AND REFRACTIVE CORRECTION

[75] Inventors: Eugene I. Gordon, Mountainside; Ernest S. Geskin, Edison; Francis A. L'Esperance, Jr., Englewood, all of N.J.

[73] Assignee: New Jersey Institute of Technology, Newark, N.J.

[21] Appl. No.: 09/320,698

[22] Filed: May 27, 1999

Related U.S. Application Data

[62] Division of application No. 08/718,347, Apr. 25, 1997.

[51] Int. Cl.$^7$ ........................................................ A61F 9/00
[52] U.S. Cl. ................................................................ 606/166
[58] Field of Search ............................. 606/166, 1, 167, 606/159, 174

[56] References Cited

U.S. PATENT DOCUMENTS

| | | | |
|---|---|---|---|
| 5,312,330 | 5/1994 | Klopotek | 606/166 |
| 5,443,473 | 8/1995 | Miller et al. | 606/174 |
| 5,935,140 | 8/1999 | Buratto | 606/166 |
| 5,947,987 | 9/1999 | Gordon et al. | 606/166 |

*Primary Examiner*—Michael Buiz
*Assistant Examiner*—Kevin Truong
*Attorney, Agent, or Firm*—Klauber & Jackson

[57] ABSTRACT

The device for benign, non-surgical external shaping of corneal tissue to compensate, by refractive correction, for deviations from normal focussing. The jet is directed to erode corneal tissue to provide an increase in curvature to correct for far-sightedness i.e., to refocus a perceived image from beyond retina onto the surface of the retina.

7 Claims, 4 Drawing Sheets

METHOD AND DEVICE FOR CORNEAL SHAPING AND REFRACTIVE CORRECTION

This Application is a Division of application Ser. No. 08/718,347, filed Apr. 25, 1997 now pending.

FIELD OF THE INVENTION

This invention relates to refractive correction, by means of corneal tissue shaping, to compensate for deviations of the imaging system of an eye from normal focussing directly on the retina of the eye, and, in particular, to non-surgical means for effecting such correction.

BACKGROUND OF THE INVENTION

Two major methods of eye cornea reshaping, are in current use, for correction of abnormal vision, resulting from improper eye focussing (generally, the conditions of myopia, with the perceived image optimal focussing in front of the retina; hypermetropia (hyperopia), with the image optimal focussing beyond the retina; and astigmatism which combines symptoms of both myopia and hyperopia, on a localized basis) The first method, radial keratotomy, involves the surgical incision of the cornea of the eye with deep medial cuts which cause a predictable flattening of the cornea of the eye when the eye heals. The reshaped cornea of the eye, with changed curvature and concomitant changed refraction, causes light or optical rays associated with an image (the perceived image), passing through the lens of the eye, to be refocussed on the retina, with refractive compensation, such as for eye shape deviations from normal. This method is however a major surgical one, and requires considerable skill in proper utilization. Improper incisions can detrimentally permanently affect the eye, without recourse to ready correction. Scarring is not uncommon and some deaths have resulted. In addition, the correction may also vary with time.

The second major method for vision correction involves the use of the excimer laser which is on the verge of FDA approval for widespread use. The excimer laser operates by controllably ablating away portions of corneal tissue, mostly through photochemical disintegration of the tissue, to either increase or decrease the effective curvature of the front of the cornea (i.e. corneal tissue), thereby correctively refocussing images on the retina. While this procedure is less invasive and traumatic than the radial keratotomy, and has had no associated injuries in over 250,000 procedures, it is nevertheless accompanied by some heat generation and dehydration, for an extended period of time. The ablation technique leaves the surface structured on a microscopic scale, and also affects adjacent corneal surface tissue and, with the plumes, results in an inaccuracy of correction of up to one diopter or more deviation from the desired value. This compares unfavorably with corrective lenses and contact lenses which provide a more accurate correction to within 0.25 diopters deviation. In addition, some haze usually results from wound healing effects.

SUMMARY OF THE INVENTION

The present invention comprises a method and device for benign, non-surgical, external shaping of surface corneal tissue to compensate, by refractive correction, for deviations in the eye imaging system which prevent normal focussing directly on the retinal plane of the eye.

The imaging system of a human eye generally comprises the cornea, pupil, lens and retina. Image focussing is effected through the cornea, pupil and lens, and the image is normally focussed directly on the surface of the retina. Focussing power for the direct imaging on the retina, is dependent to a great extent upon the shape of the front surface of the cornea (about 70% of refractive power) and to a lesser extent (30%) on the eye crystalline lens. Accordingly, small changes in the shape and effective curvature of the front surface of the cornea will effectively correct for eye imaging system deviations, to properly refocus images on the retina. The relationship of surface corneal tissue removal to appropriate correction for eye deviations from normal, has been fully developed with respect to the excimer laser, as well as with contact lenses, which do the same thing, i.e., reshape the front surface curvature of the cornea. Contact lenses however, exhibit problems of their own with respect to their own surfaces and damage to cornea.

In accordance with the present invention, a small amount of surface corneal tissue is gently but rapidly (several seconds) mechanically removed by erosion, by an imperceptibly felt, highly controlled and limited area, e.g. one or more 2–20 mils diameter wide, sterile isotonic water jets, impacting with a velocity of at least about 200 and up to about 500 meters/second, preferably at about 225–300 meters/second. Individual jets are of such 2–20 mils dimension, although a linear array of such jets can be used, having accordingly a larger overall dimension.

Erosion rate, with tissue removal, is directly related to the impact velocity and the mass of water. Thus, a lower velocity significantly increases the time for effecting the correction and a greater velocity renders the erosion more difficult to control. Impact velocity at and above 500 meters/second is conceivable but is extremely fast and requires erosion speed control with greater accuracy than currently available, in order to avoid excessive tissue removal. The use of values at the preferred range of 225–300 m/sec substantially simplifies the apparatus being used and greatly lowers cost.

Though in all instances the impact velocity is relatively high, the jet is of a very limited area at any given period of time. Accordingly, even with arrays of jets, the total impact on the eye is relatively low and the eye itself is not adversely affected. Additionally, there is little, if any, appreciable discomfort, since at most, there is a total impact force of only a few ounces, substantially less than the pressure exerted by tonometers, which eyes readily tolerate. Larger nozzle diameters can be used, but it is understood that there must be a greater degree of temporal control of the erosion rate because of the increased mass of water.

To increase effective corneal front surface curvature, resulting in a closer focal point, in correcting for hypermetropia (far-sightedness), the jet is directed primarily circumferentially about a central axis (an axis going through the center of the pupil) to erode a maximum depth of 175 microns (about 30% of corneal tissue depth, which is about 520 microns), circumference area. The preferred diameter of the circumference, having tissue removed by the erosion, should approach the maximum dilation of the pupil, of about one centimeter. The energy of the water jet is controlled, as for example by modulating the velocity of impact at the cornea tissue so as to erode the tissue along the circumference to provide differing amounts of corneal front surface curvature change, which is related to the refractive correction required. The greater the undercut, formed by the tissue erosion, the more pronounced is the curvature increase.

Alternatively, to correct for myopia (near-sightedness), a central portion of tissue or circular area (up to about 1 cm in diameter) is relatively flattened out (also with a maximum depth of flattening of about 175 microns), by erosion, to decrease effective curvature, with a displacement of the focal point from in front of the retina to the surface of the retina. The relative flattening is in increasing flatter gradations toward the center of the circular area. The amount of surface flattening is directly related to decreasing curvature and the diopter correction desired.

Astigmatism is corrected by a combination of circumferential erosion and flattening in appropriately selected areas of the corneal tissue. In all instances, there is a corrective refraction to cause images to focus properly upon the retina with minimal blurring on any portion of the image. The corrective refraction is generally a relative one, with one portion of the cornea being specifically eroded to a greater extent than another port ion, and with the changes being pre-determinately graded across the cornea.

The jet is directed by a nozzle (or array of nozzles) to to provide the desired curvature, for the refractive correction required. Preferably, for greatest accuracy, the nozzle is positioned no more than several centimeters from the eye and is used in several passes, depending upon the jet velocity, and depth of erosion required. In particular, an x-y table controlled nozzle is directed by a template movement or, more preferably, by a computer having the template as software instructions therein. The computer causes the x-y table controlled jet to follow the template via a 2-dimensional linear raster, a spiral, or similar movement until the desired diopter change is effected. Eroded tissue is washed away by the jet itself in the manner of a non-controlled eyewash.

Protective valve shut-off control may be used to provide a means for preventing overexposure of the eye to the eroding water jet by automatic shut-off of the isotonic water supply, if either erosion is complete, or if there is a sensed problem with the system. In addition, a protective mask may be used to shield the remainder of the eye from unwanted jet impingement. For additional safety, the protective mask may be a moving one with capability of entirely shielding the eye from jet impingement upon a sensing of sufficient erosion or if there is a sensed problem with the jet system.

Since there is no heating of the cornea, with concomitant chemical or thermal induced deviations, or by-products of the process to impede the jet, correction can be effected within a range of 0.25 diopters, comparable to that of corrective lenses and contact lenses. Epithelium layer regrowth occurs within several days to protect and passivate the cornea as correctively reshaped. A protective cap (contact lens) may be used during the regrowth.

It is an object of the present invention to provide a method and device for non-traumatic refractive correction of an eye using an isotonic water jet to externally reshape the front surface of the cornea.

It is a further object of the present invention to provide said method and device wherein the cornea front surface reshaping is effected with a patient perception of little more than an eyewash.

It is a still further object of the present invention to provide said method and device which utilize no heat, photochemical reaction, or invasive surgery and wherein the correction is comparable to that of corrective lenses and contact lenses.

These and other objects, features and advantages of the present invention will become more apparent from the following discussion and the drawings in which:

DETAILED DESCRIPTION OF THE INVENTION

Figure 1:
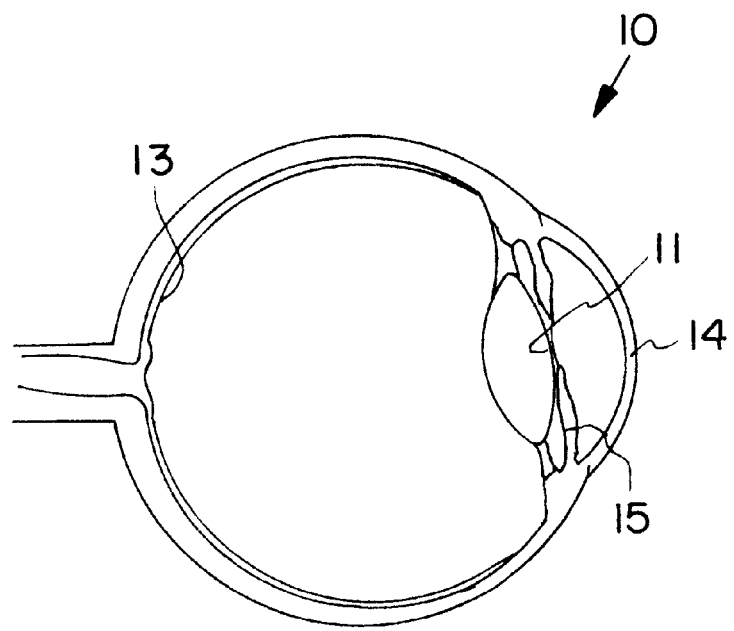
FIG. 1 is a schematic longitudinal cross section through a human eye, and illustrates the relation of the cornea to other elements of the eye.

Generally the present invention comprises the external removal of shallow portions of surface corneal tissue, by water jet erosion thereof, to refractively correct for deviations, in image focussing on the retina, caused by deviations of the imaging system of the eye from normal. The cornea front surface is minimally reshaped thereby, with either increased or decreased curvature, to properly refocus perceived images directly on the retina.

The erosion removal, as opposed to the photochemical disintegration of corneal tissue, caused by the prior art excimer laser, is effected in accordance with the present invention, without heat generation or chemical reaction, by an imperceptibly felt, highly controlled and limited area, e.g. 2 to 20 mils diameter isotonic water jet or array of such jets. An effective erosive water jet impacting with a velocity of at least about 200 to about 500, preferably 225–300 meters/second, results in a total force of no more than a few ounces, which is less than that exercised by a tonometer. The present procedure is rapid (several seconds duration), because of direct tissue contact with the water jet and is relatively benign with a patient perception of no more than an ordinary eye wash. In addition, the eroded surface is polished by the jet, in contrast to the excimer laser which produces microstructure.

Though an isotonic water jet has been described in U.S. Pat. No. 3,818,913, for removal of tissue, the device and method employed therein are designed specifically as a tissue disintegrator for use in an invasive internal surgical procedure, in completely removing unwanted growths such as cataracts, i.e. as an endoscope. The water jet in said patent is described as being adapted to be inserted directly into the eyeball, through an incision, and is used for internal tissue disintegration, such as for cataract removal rather than shaping. To this effect, the water jet is pulsed. Though a continuous fine stream is described, it is referred to as being for some undefined applications. The water jet is used in conjunction with a vacuum debris removal element and a separate irrigation source and is applied as a relatively low pressure (15 to 200 lbs/in$^2$) low velocity (50 to 500 ft/sec.) tissue disintegrator. It is however, totally unsuitable for use in shaping, by finely controlled tissue erosion, and in particular will not erode corneal tissue at such speeds.

Pursuant to the present invention portions of the corneal tissue are selectively removed by moving the water jet relative to the cornea to provide controlled removal of said portions of tissue to effect a predetermined effective curvature change at the front surface of the cornea, and thereby the desired refractive correction. Typically a predominately circumferential erosion can be effected as in FIG. 3 for increased corneal curvature or a flattening erosion as in FIG. 2 to decrease curvature. Such corneal tissue reshaping, may be effected by controlling as a function of its impact point on the corneal front surface, the velocity of the water jet proceeding from its source nozzle; the length of application time of the jet at the selected point on the corneal tissue surface; and by the masking and unmasking (by restrictive gating) of impact areas. The use of a computer to control relative movement between the jet source nozzle and the corneal surface makes such control relatively easy to effect. Alternatively, or in conjunction with computer control, a mask positioned between the nozzle or nozzles and the cornea, can be used to selectively control nozzle water jet impingement by opening and closing of one or more gates or by intermediate positions of the gates to restrict the water jets from selected nozzles. The jet or jets from the nozzle or nozzles provide the requisite erosion with the specific refractive correction required, with up to an accuracy of 0.25 diopters.

The nozzle or nozzles movement can be mechanically, or more preferably computer template controlled, in a manner similar to normal corrective lens production. The computer, in following a template of the correct curvature, effects a raster, spiral or similar movement to systematically erode the requisite areas by gradually descending deaths until the correct curvature is achieved. The computer provides instructions, in accordance with the template, to effect site-specific erosion by varying and controlling the water pressure in the one or more nozzles and/or by varying the traversing speed of the water jet or jets along the trajectory or raster, and thus the site-specific time of erosion.

The erosion, in accordance with the present invention, affects a layer of corneal tissue, of at most 175 microns, which leaves a considerable amount of tissue remaining to maintain tensile strength of the cornea, and should there be any further need for positive or negative diopter corrections.

In all embodiments, it is desirable that areas (of both the eye and the cornea) which are not to be eroded, are appropriately protectively masked against accidental impingement by the water jet.

DETAILED DESCRIPTION OF THE DRAWINGS AND THE PREFERRED EMBODIMENT

Figure 2:
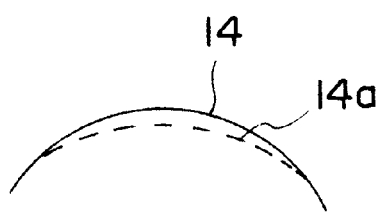
FIG. 2 schematically depicts the surgical correction that is typically effected by the invention in order to correct for myopia.
Figure 3:
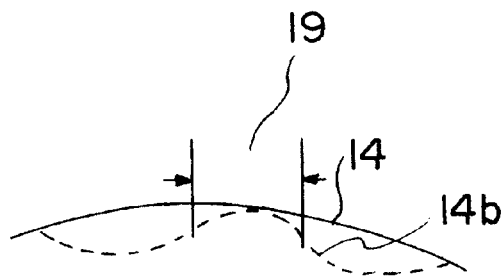
FIG. 3 schematically depicts the surgical correction that is typically effected by the invention in order to correct for hypermetropia.

With specific reference to the drawings, in FIG. 1 a human eye 10 is schematically depicted in longitudinal cross section. The eye imaging system is comprised of a lens 11, cornea 14, pupil 15, and retina 13 As is well-known, deviations in focussing of eye 10 result from eyeballs which have deformed to the point at which images no longer focus directly on retina 13. Instead, in the schematic of FIG. 2, the focussing plane of the image will be in front of the retina, resulting in a near-sighted condition. In FIG. 3, the image will be focussed beyond the plane of the retina, resulting in a far-sighted condition. The dotted lines 14a and 14b in FIGS. 2 and 3, depict the change in contour of cornea surface 14 which is typically effected by the invention in order to achieve corrected light refraction. In FIG. 3 the zone 19 represents the approximate anterior apex of the cornea vision zone, which is typically about 5–6 mm wide.

Figure 4:
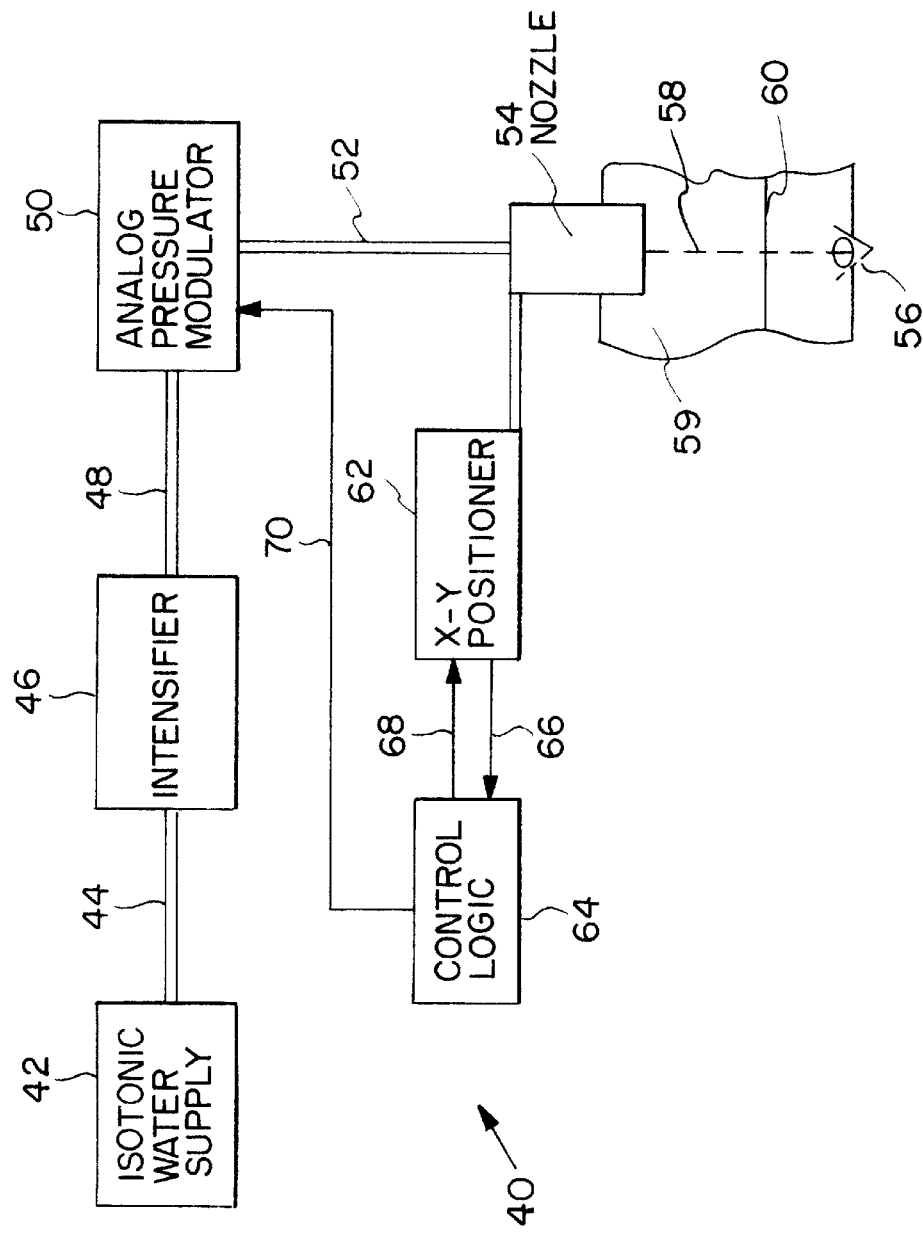
FIG. 4 is a schematic block diagram of a system in accordance with the invention being used in the course of a photorefractive keratectomy.

In FIG. 4 a schematic block diagram appears of apparatus 40 in accordance with the present invention. An isotonic water supply 42 provides water to a pressure intensifier 46 via conduit 44. The intensifier 46 is a well-known device, one type of which is available from the U.S. distributor Autoclave Company under the trade name MAXIMOTOR. The output from intensifier 46 is typically at about 5,000 to 10,000 p.s.i. Representatively at about 7500 p.s.i., it is provided via conduit 48 to the analog pressure modulator 50. The latter is a piezoelectric or other driven device which in response to electrical control signals proceeding from control logic 64 via line 70 modulates the output pressure in conduit 52 through which water flows to nozzle 54.

Nozzle 54 is movable in the X-Y plane, i.e. in the plane transverse to the plane of the drawing. The nozzle can e.g. be movable by being mounted in an X-Y table. Such movement is controlled by logic 64 through control line 68 with feedback data indicative of the X-Y position being provided to logic 68 by line 66. The water jet 58 from nozzle 54 after passing through a limiting mask 60 is seen to be rendered incident on the eye 56, more specifically at the front cornea surface which is to be subjected to the controlled erosion process.

Pursuant to a further aspect of the invention, it has been found that when the water jet 58 proceeds directly from nozzle 54 to the cornea target tissue, i.e. via a normal air path, there is a marked tendency for the jet to entrain the air or other gasses through which the jet passes. This has been found to yield detrimental results in the tissues in which the jet impacts, since the entrained gasses will be released in the tissues with damaging effects. It has now been found that this effect can be precluded by enveloping the jet in an aqueous bath in its path of transit from nozzle to tissue. This is shown in FIG. 4, in the form of an enveloping aqueous bath 59. In practice a simple cup can be used to contain the bath. The bottom of the cup is placed in fluid tight relation to the eye undergoing treatment, with the remote end of the cup being open to receive the tip of nozzle 54.

In the course of operating system 40 a reference position for the impacting jet on the target cornea is initially established, and this information is provided to control logic 64 The nozzle is then moved in the X-Y plane so as to provide jet impact on successive points of the corneal front surface, during which movement the pressure in conduit 54 is modulated by modulator 50. This in turn provides a corresponding modulation in the velocity of the water jet 58. The displacement of jet 58 can be in the form of a scan such as a raster scan. Thus the depth of erosion at the cornea tissue is precisely controlled over the course of a scan, to in turn shape the surface of the cornea acted upon into the form appropriate for the desired refractive correction.

In operation, the head of the patient is held in position and the eyelid (of eye 10) is held open, with the patient being directed to fix focus on a pre-selected spot, as with use of an ophthalmological tonometer or an excimer laser. The eye is protectively masked with mask 60, with a maximum aperture equal to the dilated size of pupil 15. The appropriate nozzle or nozzle array is fixed into position, up to a few centimeters distant from and adjacent the cornea 14. Rapid movement of the appropriate shaping nozzle is effected in conjunction with an application template or with computer raster scanning control, with preprogrammed shaping parameters.

In order to enhance the safety of operation of the system 40 of the present invention, protection valves can be provided in conduit 44 which serve to automatically shut off the water supply from water reservoir 42 to the intensifier 46, and thus shut off of the eroding jet. Additional protection valves can also be placed in series with the first mentioned valves for enhanced protection and serve to interrupt the water flow, when duration of the treatment exceeds requirements. To enhance fail-safe operation all three valves can operate from separate independent pneumatic and electric activators which are controlled by independent timers (not shown). Mask 60 also functions as an additional safety element by controlling the time and area of the exposure of the cornea to the pressurized water jet.

EXAMPLE 1

In order to demonstrate the effectiveness of the method and device of the present invention, the corneal tissue of a removed pig's eye was eroded with a water jet having an impact velocity of 300–500 meters/second. Corneal tissue was removed within several seconds, with a maximum depth of 40 microns and light was internally refocussed within the pig's eye in accordance with changed cornea front surface curvature, as effected by the erosion.

EXAMPLE 2

Figure 5:
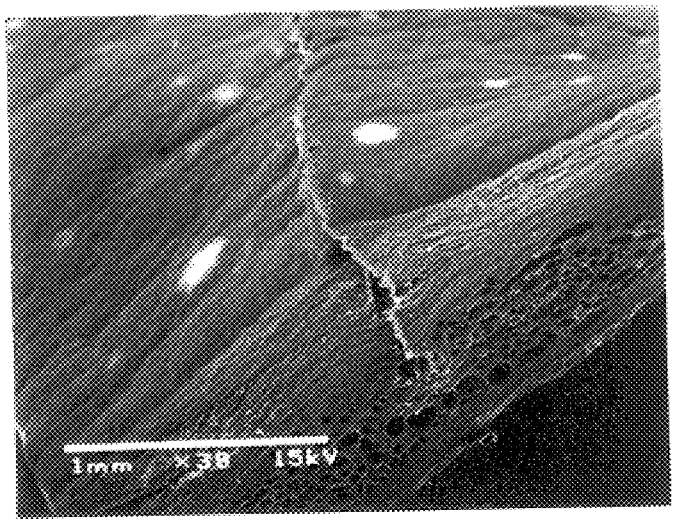
FIGS. 5 and 6 are photomicrographs of corneal sections which have been cut or eroded with a water jet which lacked the gas entrainment preclusion feature of the present invention.
Figure 6:
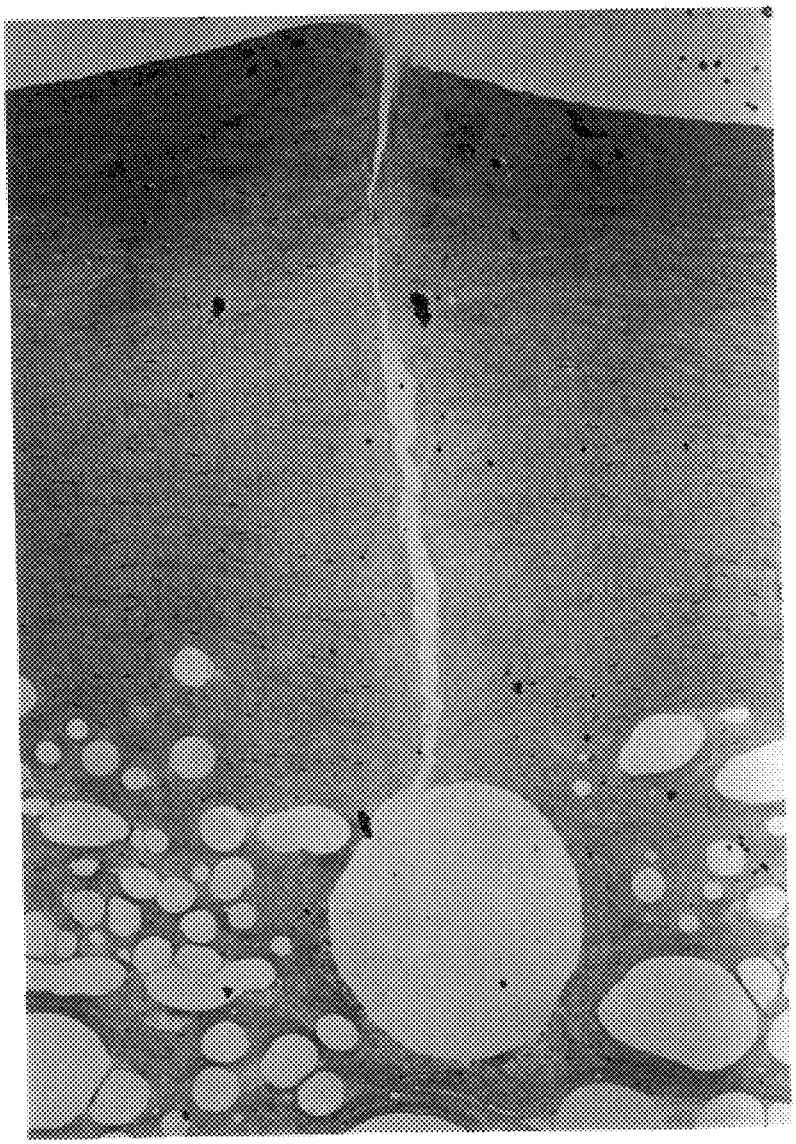
Figure 7:
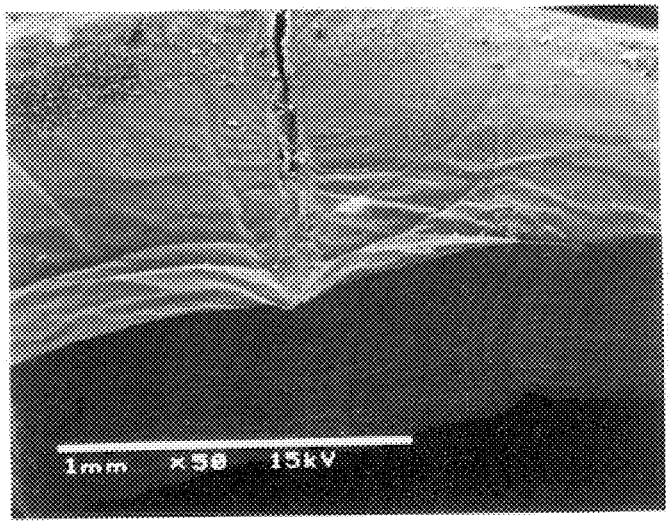
FIGS. 7 and 8 are photomicrographs of corneal sections which have been cut or eroded with a water jet which included the gas entrainment preclusion feature of the present invention.
Figure 8:
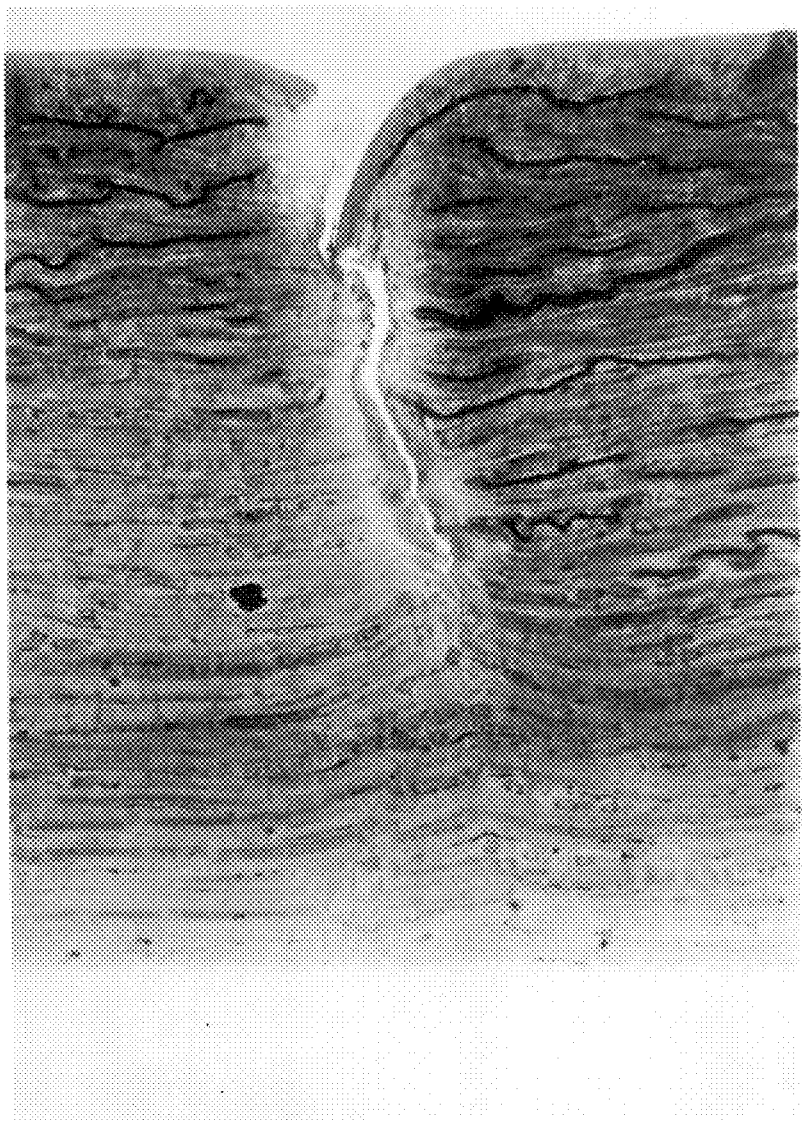

In FIGS. 5 and 6 photomicrographs depict the results of utilizing a system as in FIG. 4 in the course of providing an erosion or cut in a pig's eye FIG. 4 is an enlargement of the view of FIG. 3. The cut or erosion was effected with a jet velocity of about 250 m/sec. The jet proceeded from the nozzle 54 via an air path, i.e. the water enveloping bath 59 of FIG. 4 was not used. The surface of the cornea is apparent in the upper part of the photograph, with a transverse section of the cornea being seen at the lower right. While the cut is relatively smooth, a vast number of air bubbles or inclusions are seen to have formed at the lower reaches of the tissue. These inclusions would be detrimental to the cornea from a viewpoint of short term effect on light transmission and thus of vision. Although the inclusions will eventually dissipate, they will leave in their wake damaged tissue.

EXAMPLE 3

This Example differs from Example 2 only in that the fluid or aqueous coupling bath 59 of FIG. 4 was used in the course of otherwise identically eroding or cutting a further specimen of pig's eye. It will be seen that an extremely clean and uniform erosion or cut has resulted. Of particular significance is the complete absence of the bubbles or gas inclusions which were formed in the tissue in the procedure of Example 2. In the present instance the tissue is clear of any inclusions which would impair light transmission or create undesired refraction.

It is understood that the above Example and drawings are illustrative of the present invention and that details contained therein are not to be construed as limitations on the present invention. Thus, while refractive corrections for near-sighted and far-sighted conditions have been illustrated, refractive corrections for astigmatism can be similarly made by combination of erosion corrections. In addition, changes in jet application, jet composition, velocity, specific movement, as well as nozzle configuration, overall structure, and the like can be made without departing from the scope of the present invention as defined in the following claims.

What is claimed is:

1. A system for effecting a refractive keratectomy upon corneal tissue, comprising:

water supply means;

nozzle means connected to said water supply means and being positionable with respect to a spaced target cornea to form a water jet having a diameter at the cornea tissue target of from 2 to 20 mils diameter;

positioning means for controllably displacing the impact point of said jet upon said cornea tissue to conform to a desired pattern;

means for controlling the mechanical energy transferred by said jet at each point of its impact with said tissue, to thereby effect controlled erosion of said tissue at the said points to enable a required refractive correction; and a liquid coupling means between said nozzle means and the target cornea tissue, for surrounding and enveloping said water jet in a liquid bath to thereby preclude entrainment of tissue-damaging gasses by the said jet.

2. A system in accordance with claim 1, wherein said means for controlling the energy transferred to said tissue, comprises means for controlling the pressure of said water jet as a function of its point of impact on said tissue.

3. A system in accordance with claim 2, wherein said pressure control means modulates the pressure to achieve an impact velocity at said tissue in the range of 225 to 300 m/sec.

4. A system in accordance with claim 2, wherein said positioning means effects a scan pattern of said jet over said cornea tissue.

5. A system in accordance with claim 1, wherein said coupling means comprises a cup for surrounding in water tight relationship the eye of a patient who is undergoing said keratectomy, said cup being open at its end remote from said eye to receive the said nozzle means in the liquid containable therein.

6. In a system for effecting refractive correction for deviations of an eye imaging system comprised of a cornea with an exposed front surface; a pupil; a lens; and a retina; from focusing perceived images directly on the retina of the eye; said system comprising means for removing selected external portions of tissue from the front surface of the cornea, in an area defined by a maximum dilation of the pupil of the eye, whereby curvature of the front surface of the cornea is changed to a sufficient extent, whereby light rays from any point in a perceived image, passing through the cornea and the lens, are substantially optimally focused thereafter on the retina; THE IMPROVEMENT COMPRISING:

said means for removing said selected portions of said tissue comprises means for impinging said tissue with at least one water jet having an impact velocity of at least 200 meters/second; and means for moving the water jet relative to the cornea to provide controlled removal of said portions of tissue to effect said change in curvature at the front surface of the cornea.

7. A system in accordance with claim 6, further comprising:

water supply means;

nozzle means connected to said water supply means and being positionable with respect to a spaced target cornea to form a said water jet having a diameter at the cornea tissue target of from 2 to 20 mils diameter; and a liquid coupling means between said nozzle means and the target cornea tissue, for surrounding and enveloping said water jet in a liquid bath to thereby preclude entrainment of tissue-damaging gasses by the said jet.

* * * * *